United States Patent
Taya et al.

(10) Patent No.: US 6,756,198 B2
(45) Date of Patent: Jun. 29, 2004

(54) OLIGONUCLEOTIDE FOR HIGHLY SENSITIVE DETECTION OF HEPATITIS C VIRUS AND METHOD FOR DETECTION THEREOF

(75) Inventors: Toshiki Taya, Kanagawa (JP); Takahiko Ishiguro, Kanagawa (JP); Juichi Saito, Kanagawa (JP)

(73) Assignee: Tosoh Corporation, Yamaguchi (JP)

( * ) Notice: Subject to any disclaimer, the term of this patent is extended or adjusted under 35 U.S.C. 154(b) by 0 days.

(21) Appl. No.: 09/984,316

(22) Filed: Oct. 29, 2001

(65) Prior Publication Data

US 2002/0123038 A1 Sep. 5, 2002

(30) Foreign Application Priority Data

Oct. 30, 2000 (JP) ..................... P. 2000-334945

(51) Int. Cl.[7] .......... C12Q 1/70; C12P 19/34; C07H 21/04; C12N 15/00
(52) U.S. Cl. .......... 435/5; 435/3; 435/4; 435/6; 435/7.2; 435/7.9; 435/8; 435/7.91; 536/24.3; 536/24.32; 536/24.33
(58) Field of Search .............. 435/3, 4, 5, 6, 435/7.21, 7.9, 8, 7.91; 536/24.3, 24.32, 24.33

(56) References Cited

U.S. PATENT DOCUMENTS 5,882,852 A * 3/1999 Bukh et al. ............ 435/5

6,485,903 B1 * 11/2002 Mayrand ................ 435/6

OTHER PUBLICATIONS

Lunel et al. J.Virol. Methods 1995, vol. 54, pp. 159–171.*

Roche Molecular Biochemicals 1999, Biochemicals catalog pp. 230–231.*

Kato et al., "Molecular cloning of the human hepatitis C virus genome from Japanese patients with non–A, non–B hepatitis", *Proc. Natl. Acad. Sci.*, vol. 87, pp. 9524–9528, Dec. 1990.

* cited by examiner

*Primary Examiner*—James Housel
*Assistant Examiner*—Bao Qun Li
(74) *Attorney, Agent, or Firm*—Piper Rudnick LLP; Steven B. Kelber (57) ABSTRACT

An oligonucleotide useful for specific amplification of HCV RNA, or highly sensitive detection and identification of HCV RNA, and a combination thereof. A detection method using RNA amplification step, wherein the oligonucleotide of SEQ ID NO: 11 is used as a first primer and the oligonucleotide of SEQ ID NO: 6 or 7 as a second primer, the oligonucleotide of SEQ ID NO: 12 is used as a first primer and the oligonucleotide of SEQ ID NO: 7 as a second primer, or the oligonucleotide of SEQ ID NO: 13 is used as a first primer and the oligonucleotide of SEQ ID NO: 9 as a second primer.

2 Claims, 4 Drawing Sheets

OLIGONUCLEOTIDE FOR HIGHLY SENSITIVE DETECTION OF HEPATITIS C VIRUS AND METHOD FOR DETECTION THEREOF

FIELD OF THE INVENTION

The present invention relates to an oligonucleotide effective in detecting Hepatitis C virus (hereinafter, referred to as "HCV") at clinical laboratory tests and diagnoses, and to a method for detecting HCV using the oligonucleotide.

BACKGROUND ART

HCV infection has been hitherto known as non-A non-B type infection, and is a non-oral infection caused by blood transfusion and the like. Although the HCV infection has a possibility of inducing a persistent and serious liver disease, the therapeutic method has not yet been established, so that the infection has been a big medical problem. Therefore, it is important to find out the infection in its early stages, to treat it properly, or not to use infected blood at transfusion. For the purposes, it becomes an important problem to establish an accurate and rapid detecting method at clinical laboratory tests.

As a method for determining whether the abnormality of liver function is due to HCV or not, an antibody test (enzymatic immunoadsorption method) is known. However, in such a method for detecting anti-HCV antibody, it is impossible to diagnose in its early stages before the antibody is produced. Thus, more highly effective test method is desired at actual clinical site.

HCV is a single-stranded RNA virus comprising about 9000 nucleotide, and the most sensitive test for HCV is to measure directly the virus RNA in blood. The base sequence of HCV selected from Japanese hepatitis C patients is already known (Kato et al., Proc. Natl. Acad. Sci. USA, 87, 9524–9528 (1990) and so forth). Thus, hybridization method is attempted for detection and identification of HCV using a gene probe specific to HCV RNA. In this case, the gene probe is designed so as to bind specifically to the non-translation region at the 5' end or 3' end of the RNA.

As described above, in antibody test, it is impossible to diagnose in its early stages of the infection, a complex operation and a long period of time are required, and also it is difficult to detect a very small amount of HCV present in a sample for a short period of time, so that it is desired to develop more rapid and highly sensitive detection method. Furthermore, in order to test more conveniently, it is required to develop an automated test apparatus.

On the other hand, for highly sensitive detection, it is preferable to detect a specific sequence of a gene to be detected and identified or an RNA derived from the gene, after their amplification.

As a method for amplifying a specific sequence of RNA of a genome such as HCV, reverse transcription-polymerase chain reaction (RT-PCR) method is known. The method comprises synthesizing CDNA of a target RNA in reverse transcription step and successively amplifying a specific DNA sequence by polymerase chain reaction wherein a cycle of thermal denaturation, primer annealing, and elongation reaction are repeatedly carried out at both ends of the specific sequence of cDNA in the presence of one pair of primers complementary to and homogeneous to the both ends and a heat-resistant DNA polymerase. However, RT-PCR method requires tedious operations, and rapid elevation and lowering of temperature are repeated, which inhibits automation of the method.

As amplification methods for a specific RNA sequences, other than RT-PCR method, there are known NASBA method, 3SR method, and the like wherein a specific RNA sequence is amplified by a synergistic action of a reverse transcriptase and an RNA polymerase. In the methods, a chain reaction is carried out wherein a double-stranded DNA containing a promoter sequence is synthesized toward a specific sequence of the target RNA by a primer containing a promoter sequence, a reverse transcriptase, and ribonuclease H, then, an RNA containing the above specific base sequence is synthesized by an RNA polymerase using the double-stranded DNA as a template, and also the RNA successively acts as a template for synthesizing the double-stranded DNA containing the promoter sequence. NASBA method or 3SR method enables nucleic acid amplification at a constant temperature, and thus, is considered to be suitable for automation. In this case, it is possible to determine the presence of HCV and also the amount thereof by qualifying or quantifying HCV RNA.

Amplification of the above specific sequence by NASBA method or the like requires an oilgonucleotide having a high specificity with the above specific sequence. Furthermore, for highly sensitive detection and identification thereof, an oligonucleotide having a high specificity with the target RNA is required. However, since the reaction is carried out at a relatively low temperature (e.g., 41° C.) in NASBA method or the like, there is a possibility that the target RNA forms an intramolecular structure which inhibits binding of a primer and thus lowers reaction efficiency. Therefore, an operation for enhancing the binding efficiency of the primer is needed wherein the target RNA is subjected to thermal denaturation before the amplification reaction so as to break the intramolecular structure of the target RNA. Furthermore, also in the case of detecting RNA at a low temperature, an oligonucleotide capable of binding to the RNA which has formed the above intramolecular structure is required.

SUMMARY OF THE INVENTION

Thus, object of the invention is to provide an oligonucleotide useful for specific cleavage and amplification of HCV RNA, and more highly sensitive detection and identification thereof than in the conventional method, particularly, to provide an oligonucleotide useful for specific amplification of the RNA at a relatively low temperature (e.g., 41° C.) and highly sensitive detection and identification thereof. Another object of the invention is to provide a method for amplifying the RNA using a suitable combination of such oligonucleotides and further detecting the RNA.

The first embodiment of the present invention which achieves the above-mentioned objects relates to an oligonucleotide useful for cleaving, detecting, or amplifying HCV RNA, which is capable of binding to a specific site of HCV RNA at a relatively low temperature and a constant temperature (35 to 50° C., preferably 41° C.) and comprises at least 10 continuous bases in any one of the sequences shown in SEQ ID NOS: 1 to 10.

The second embodiment of the invention relates to the oligonucleotide according to above first embodiment, wherein the oligonucleotide is an oligonucleotide probe for cleaving the RNA at the specific site by binding of part of the above oligonucleotide to the specific site of the RNA. The third embodiment of the invention relates to the oligonucleotide according to above first embodiment, wherein the nucleotide is an oligonucleotide primer for DNA elongation reaction. The invention of fourth embodiment of the invention relates to the oligonucleotide according to above first embodiment, wherein the nucleotide is an oligonucleotide probe modified partially or labeled with a detectable labeling substance.

The fifth embodiment of the invention relates to an amplification step which comprises:

forming an RNA-DNA duplex by forming a cDNA by the action of an RNA-dependent DNA polymerase using a specific sequence of RNA derived from HCV in a sample as a template, a first primer having a sequence homologous to the specific sequence, and a second primer having a sequence complementary to the specific sequence (wherein either primer of the first or second primers has an sequence to which a promoter sequence of an RNA polymerase is added at the 5' end), forming a single-stranded DNA by degrading the RNA-DNA duplex by ribonuclease H, forming a double-stranded DNA having a promoter sequence capable of transcribing an RNA comprising the above RNA sequence or a sequence complementary to the above RNA sequence by a DNA-dependent DNA polymerase using the single-stranded DNA as a template, and forming an RNA transcription product from the double-strand DNA in the presence of an RNA polymerase, the RNA transcription product successively acting as a template for the formation of the single-stranded DNA by the above RNA-dependent DNA polymerase, wherein the oligonucleotide of SEQ ID NO: 11 is used as the first primer and the oligonucleotide of SEQ ID NO: 6 or 7 as the second primer, the oligonucleotide of SEQ ID NO: 12 is used as the first primer and the oligonucleotide of SEQ ID NO: 7 as the second primer, or the oligonucleotide of SEQ ID NO: 13 is used as the first primer and the oligonucleotide of SEQ ID NO: 9 as the second primer.

The sixth embodiment of the invention relates to the amplification step according to above fifth embodiment, wherein the above first primer is an oligonucleotide comprising at least 10 continuous bases of the sequence of SEQ ID NO: 11, 12, or 13. The seventh embodiment of the invention relates to amplification step according to the fifth embodiment, wherein the above second primer is an oligonucleotide comprising at least 10 continuous bases of the sequence of SEQ ID NO: 6, 7, or 9. The invention of eighth embodiment of the invention relates to a method for detecting HCV RNA according to the fifth embodiment comprising measurement of fluorescent strength of a reaction solution, wherein the above RNA-amplification step is carried out in the presence of an oligonucleotide probe labeled with an intercalative fluorescent pigment, the sequence of the probe being complementary to at least part of the RNA transcription product, and the fluorescent characteristic of the probe being changed by the complementary binding to the RNA transcription product as compared with the case that the complex is not formed. The following will explain the invention in detail.

BRIEF DESCRIPTION OF THE DRAWINGS

FIG. 4 is graphs illustrating relationship between reaction time and increasing rate of fluorescence in Example 3. In the figure, the word "10000 copies" means the case that initial RNA amount of $10^4$ copies/5 μl was used as the RNA sample, the word "1000 copies" means the case that initial RNA amount of $10^3$ copies/5 μl was used as the RNA sample, and N means the case that the diluent alone was used instead of the RNA sample.

At the above-mentioned amplification of the RNA, the oligonucleotide of the invention is an oligonucleotide which specifically forms a complementary binding to a region free from an intramolecular structure of the target RNA, and is capable of binding specifically to the target RNA without the above-mentioned thermal denaturation. As mentioned above, the invention relates to an oligonucleotide which binds to a region free from the intramolecular structure of HCV RNA at a relatively low temperature and a constant temperature (35 to 50° C., preferably 41° C.), and also an oligonucleotide useful for specific cleavage, amplification, or detection of HCV RNA. More specifically, the invention relates to an oligonucleotide for cleaving the above target RNA at a specific position, an oligonucleotide primer for amplifying the above target DNA by PCR method, an oligonucleotide primer for amplifying the above target RNA by NASBA method or the like, and an oligonucleotide for achieving a rapid and highly sensitive detection by using an oligonucleotide for detecting the target nucleic acid without such amplification or after such amplification.

Moreover, the invention provides, through providing a combination of oligonucleotides for amplifying and detecting HCV RNA at a relatively low temperature and a constant temperature (35 to 50° C., preferably 41° C.), i.e., a combination of oligonucleotide primers for amplifying HCV RNA, a method for a convenient, rapid, and highly sensitive detection of HCV RNA and a detection kit using the same for clinical laboratory tests and the like.

SEQ ID NOS: 1 to 13 show some examples of the oligonucleotide of the invention useful for cleavage, amplification, or detection of HCV RNA. HCV RNA herein includes RNAs to be prepared using these genes as templates. The oligonucleotides of the invention may be those containing whole base sequences described as SEQ ID NOS: 1 to 13, respectively, but since about 10 bases are sufficient for specific binding to HCV RNA and the like, the oligonucleotides may be oligonucleotides comprising at least 10 bases in the sequences described respectively, and furthermore, may be oligonucleotides complementary thereto.

The oligonucleotide of the invention can be used, for example, as a probe for cleavage of an RNA. Cleavage of a target RNA at a specific position may be effected by hybridizing an oligonucleotide of the invention to the single-stranded target RNA and treating it with an enzyme which cleaves only the RNA of heteroduplex part of RNA-DNA. As the enzymes, those known as enzymes having ribonuclease H activity may be used.

The oligonucleotide of the invention can be employed, for example, as an oligonucleotide primer for amplification of a nucleic acid. When a nucleic acid amplification method is carried out using the oligonucleotide of the invention as a primer, only the target nucleic acid, i.e., HCV RNA can be amplified. Examples of the amplification method include PCR method, LCR method, NASBA method, 3SR method, and the like. Among them, the nucleic acid amplification methods such as LCR method, NASBA method, and 3SR method are preferred since they can be carried out at a constant temperature. The detection of the amplification product by various methods enables the detection of HCV RNA. In this case, the above oligonucleotide other than the oligonucleotide employed in the amplification may be used as a probe for the detection, or the fragments of the specific sequence amplified may be confirmed by electrophoresis or the like.

The oligonucleotide of the invention can be used as a detection probe through partial modification thereof or labeling with a detectable labeling substance. In the case of detecting the target nucleic acid, the oligonucleotide of the invention labeled with a detectable labeling substance may be hybridized to the single-stranded target nucleic acid and then the above label may be detected in the hybridized probe. The detection of the label may be effected by adopting a suitable method for the labeling substance. For example, in the case that an intercalative fluorescent pigment is used as the label of the oligonucleotide, only the hybridized probe can be easily detected, without removing the probe which is not hybridized to the target nucleic acid, by using a pigment or the like having a property that the fluorescent strength is increased by intercalation to the double-stranded nucleic acid comprising the target nucleic acid and the oligonucleotide probe. In the case that usual fluorescent pigment or the like is used as the label, the detection may be effected after the removal of the probe which is not hybridized to the target nucleic acid. By the way, at the detection, it is desirable to amplify the target nucleic acid in a sample to the amount detectable by various nucleic acid amplification methods such as PCR method, NASBA method, and 3SR method. Among them, most preferred is a constant-temperature nucleic acid amplification method such as NASBA method or 3SR method. In the case that the probe with which the above oligonucleotide is labeled is co-existed in the reaction solution at the amplification, it is particularly desirable to subject the probe to modification, for example, addition of glycolic acid at the 3' end so that the probe does not act as a nucleotide primer.

In one example of the embodiment of the invention, an RNA-DNA duplex is formed by effecting complementary binding of a second primer (a sequence complementary to 3' end region of a specific sequence of the target RNA) using a specific sequence of HCV RNA present in a sample as a template and forming a cDNA through elongation reaction by an RNA-dependent DNA polymerase, and then a single-stranded DNA is prepared by degrading the RNA-DNA duplex by ribonuclease H. Thereafter, a double stranded DNA having a promoter capable of transcribing an RNA comprising a sequence homologous to the above target RNA is prepared by effecting complementary binding of a first primer (a sequence homologous to the 5' end region of the target RNA, to which a promoter sequence of an RNA polymerase is added at the 5' end) to the single-stranded DNA and treating the resulting DNA with a DNA-dependent DNA polymerase. Then, an RNA transcription product comprising a sequence homologous to the above target RNA is amplified from the double-stranded DNA in the presence of an RNA polymerase. In the invention, the oligonucleotide of SEQ ID NO: 11 is used as the first primer and the oligonucleotide of SEQ ID NO: 6 or 7 as the second primer; the oligonucleotide of SEQ ID NO: 12 is used as the first primer and the oligonucleotide of SEQ ID NO: 7 as the second primer; or the oligonucleotide of SEQ ID NO: 13 is used as the first primer and the oligonucleotide of SEQ ID NO: 9 as the second primer. The first and second primers may be full length oligonucleotide of each SEQ ID NO, but a combination of oligonucleotides comprising at least continuous 10 bases of each sequence may be used.

In the above one embodiment of the invention, the target RNA should be cleaved at the 5' end of the specific sequence. As the method for cleaving the target RNA in such a manner, preferred is a method for cleaving the target RNA by ribonuclease H or the like with adding an oligonucleotide having a sequence complementary to the region redundantly adjacent to the 5' end of the specific sequence (an oligonucleotide probe for cleavage). It is desirable to use an oligonucleotide for cleavage wherein the 3' end thereof is treated so as not to act as an oligonucleotide primer, for example, an aminated oligonucleotide.

In the above one embodiment of the invention, it is preferred to carry out the amplification step in the presence of an oligonucleotide probe labeled with an intercalative fluorescent pigment having a sequence complementary to at least part of the sequence of the RNA transcription product to be amplified (an oligonucleotide probe for detection). At that time, the fluorescent characteristic of the probe is changed by the complementary binding to the RNA transcription product as compared with the case that the complex is not formed, and thus the measurement of the fluorescent strength of a reaction solution is effective. Furthermore, in the case that a labeled oligonucleotide probe is co-existed during the amplification step, it is particularly desirable to modify the probe so as not to act as a primer for elongation reaction, for example, to modify it by adding glycolic acid to the 3' end. As the oligonucleotide probe for detection, the use of the oligonucleotide having a sequence described in SEQ ID NO: 10 may be exemplified.

In another embodiment of the invention, an RNA-DNA duplex is formed by effecting complementary binding of a second primer (a sequence complementary to the target RNA, to which a promoter sequence of an RNA polymerase is added at the 5' end) using a specific sequence of HCV RNA present in a sample as a template and forming a cDNA through elongation reaction by an RNA-dependent DNA polymerase, and then a single-stranded DNA is prepared by degrading the RNA-DNA duplex by ribonuclease H. Thereafter, a double stranded DNA having a promoter capable of transcribing an RNA comprising a sequence homologous to the above target RNA is prepared by effecting complementary binding of a first primer (a sequence homologous to the 5' end region of the target RNA) to the single-stranded DNA and treating the resulting DNA with a DNA-dependent DNA polymerase. Then, an RNA transcription product comprising a sequence homologous to the above target RNA is amplified from the double-stranded DNA in the presence of an RNA polymerase. In the invention, the oligonucleotide of SEQ ID NO: 11 is used as the first primer and the oligonucleotide of SEQ ID NO: 6 or 7 as the second primer, the oligonucleotide of SEQ ID NO: 12 is used as the first primer and the oligonucleotide of SEQ ID NO: 7 as the second primer, or Gil the oligonucleotide of SEQ ID NO: 13 is used as the first primer and the oligonucleotide of SEQ ID NO: 9 as the second primer. The first and second primers may be full length oligonucleotide of each SEQ ID NO, but a combination of oligonucleotides comprising at least continuous 10 bases of each sequence may be used.

In the above one embodiment of the invention, it is preferred to carry out the amplification step in the presence of an oligonucleotide probe labeled with an intercalative fluorescent pigment having a sequence complementary to at least part of the sequence of the RNA transcription product to be amplified (an oligonucleotide probe for detection). At that time, the fluorescent characteristic of the probe is changed by the complementary binding to the RNA transcription product as compared with the case that the complex is not formed, and thus the measurement of the fluorescent strength of a reaction solution is effective. Furthermore, in the case that a labeled oligonucleotide probe is co-existed during the amplification step, it is particularly desirable to modify the probe so as not to act as a primer for elongation reaction, for example, to modify it by adding glycolic acid to the 3' end. As the oligonucleotide probe for detection, the use of the oligonucleotide having a sequence described in SEQ ID NO: 10 may be exemplified.

The following will explain the invention in further detail with reference to Examples, but the invention is not limited to these Examples.

EXAMPLE 1

It was confirmed that the oligonucleotide of the invention bound to HCV RNA specifically at 41° C. By the way, HCV RNA means an RNA synthesized by in vitro transcription using a double-stranded DNA containing the base sequence of HCV as a template and purified.

(1) A sample of a standard RNA (1552 mer) containing base numbers 1 to 1487 of HCV RNA (the base numbers of RNA are indicated according to Kato et al., "Proc. Natl. Acad. Sci. USA, 87, 9524–9528 (1990)) was quantified from ultraviolet absorption at 260 nm, and then diluted to $1.0 \times 10^{-12}$ mol/µl with an RNA diluent (10 mM Tris-HCl (pH 8.0), 0.1 mM EDTA, 0.5 U/µl RNase Inhibitor).

Then, the following reagents were dispensed into each 0.5 ml PCR tube (trade name: Gene Amp Thin Walled Reaction Tubes, manufactured by Perkin Elmer).

0.90 µl of 1 M Tris-HCl buffer solution (pH 8.6)
0.20 µl of 1 M magnesium chloride
0.67 µl of 2 M potassium chloride
0.15 µl of 0.1 M DTT
0.33 µl of 119 U/µl RNase Inhibitor
8.75 µl of distilled water
0.6 µl of 1 pmol/µl HCV RNA sample
2.4 µl of 1.0 µM oligonucleotide solution By the way, as the nucleotide solution, any one of the following oligonucleotide solutions was used.

1. An oligonucleotide complementary to base numbers 338 to 358 of HCV RNA, SEQ ID NO: 1;
2. An oligonucleotide complementary to base numbers 356 to 375 of HCV RNA;
3. An oligonucleotide complementary to base numbers 384 to 403 of HCV RNA;
4. An oligonucleotide complementary to base numbers 441 to 460 of HCV RNA;
5. An oligonucleotide complementary to base numbers 509 to 528 of HCV RNA;
6. An oligonucleotide complementary to base numbers 570 to 592 of HCV RNA, SEQ ID NO: 2;
7. An oligonucleotide complementary to base numbers 680 to 700 of HCV RNA, SEQ ID NO: 3;
8. An oligonucleotide complementary to base numbers 723 to 742 of HCV RNA, SEQ ID NO: 4;
9. An oligonucleotide complementary to base numbers 817 to 836 of HCV RNA, SEQ ID NO: 5;
10. An oligonucleotide complementary to base numbers 851 to 870 of HCV RNA, SEQ ID NO: 6;
11. An oligonucleotide complementary to base numbers 924 to 943 of HCV RNA;
12. An oligonucleotide complementary to base numbers 945 to 964 of HCV RNA, SEQ ID NO: 7;
13. An oligonucleotide complementary to base numbers 979 to 998 of HCV RNA, SEQ ID NO: 8;
14. An oligonucleotide complementary to base numbers 1012 to 1031 of HCV RNA;
15. An oligonucleotide complementary to base numbers 1054 to 1074 of HCV RNA;
16. An oligonucleotide complementary to base numbers 1137 to 1156 of HCV RNA;
17. An oligonucleotide complementary to base numbers 1176 to 1197 of HCV RNA, SEQ ID NO: 9.

(2) The above reaction solution was maintained at 41° C. for 5 minutes and then, 1 µl of a solution containing AMVR-Tase (manufactured by Takara Shuzo) was added thereto (AMVRTase is an enzyme which cleaves the RNA of a double-stranded DNA-RNA), followed by maintaining the PCR tube at 41° C. for 5 minutes.

(3) For confirming the cleaved fragments after the reaction, electrophoresis on a polyacrylamide gel (concentration of acrylamide is 5% and that of urea is 7 M) was carried out. After the electrophoresis, the gel was stained with SYBR Green II (manufactured by Takara Shuzo). Through the binding of the oligonucleotide to a specific site of the target RNA, the RNA of the DNA-RNA duplex was cleaved by ribonuclease H activity of AMVRTase and specific bands were observed.

Figure 1:
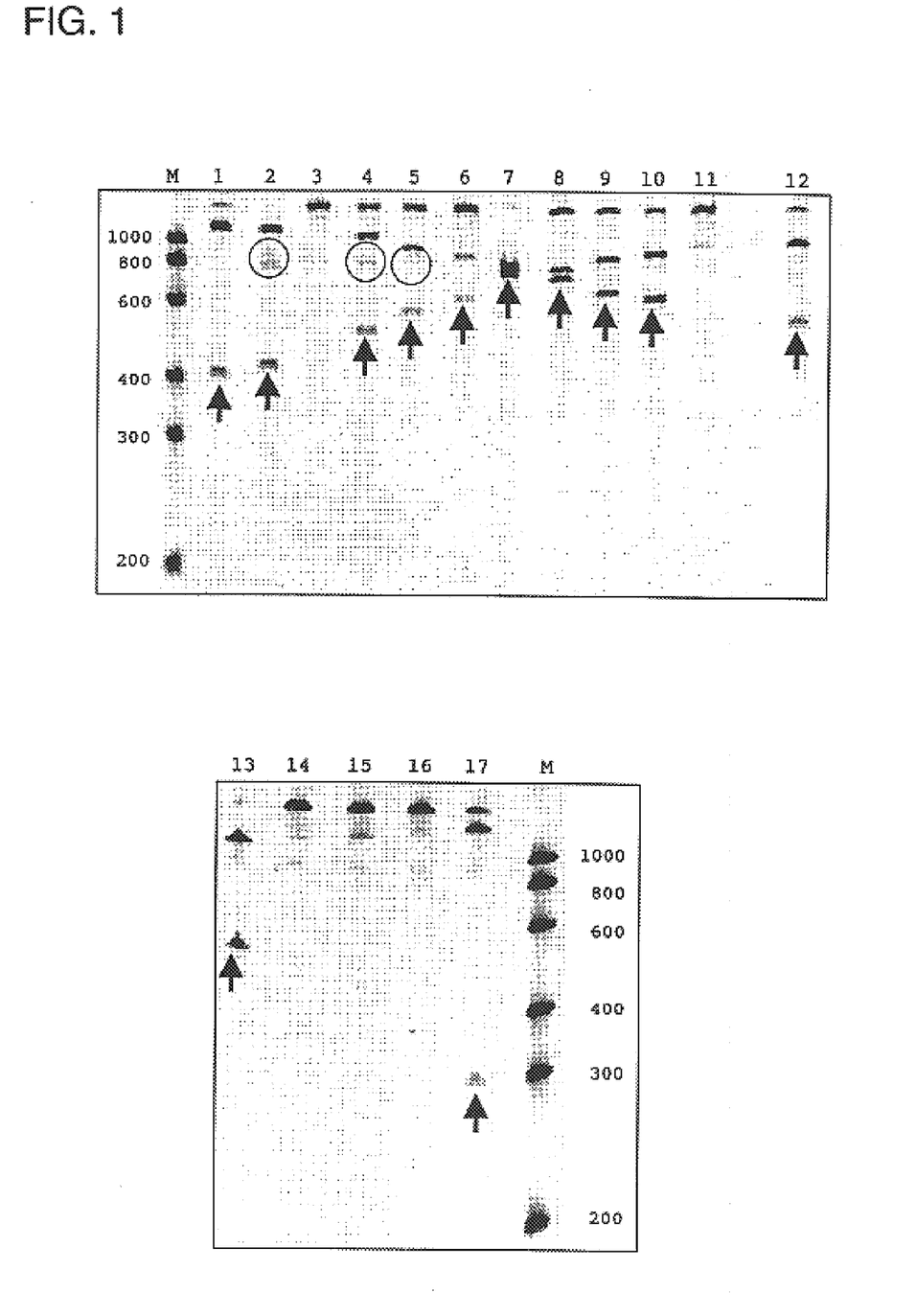
FIG. 1 is a photograph illustrating the state of the oligonucleotides (black and white were reversed), and a photograph of electrophoresis of the samples on 7 M urea-5% polyacrylamide gel after binding experiment to HCV RNA at 41° C. using oligonucleotides designed toward an intramolecular structure-free region of HCV RNA. In the figure, lane M is concerned with an RNA marker, and each number of lanes 1 to 17 indicates each number of oligonucleotide solutions shown in Example 1.

The results of the electrophoresis are shown in FIG. 1 (FIG. 1 is a photograph (black and white are reversed) illustrating the state of each oligonucleotide). Among the newly appeared bands in each lane, a band showing shorter length is indicated by an arrow in each lane where two bands resulting from specific cleavage with one oligonucleotide used were observed. In addition, remarkable non-specifically cleaved bands are circled. From these results, only in the cases that oligonucleotide solutions containing SEQ ID NOS: 1 to 9 were used, specifically cleaved bands without remarkable non-specifically cleaved bands were confirmed. Therefore, it was shown that all these oligonucleotides strongly bound to specific sites of HCV RNA at 41° C.

EXAMPLE 2

Using combinations of oligonucleotide primers according to the invention, specific amplification of the target RNA was carried out. By the way, HCV RNA means an RNA synthesized by in vitro transcription using a double-stranded DNA containing the base sequence of HCV as a template and purified.

(1) A sample of a standard RNA (1552 mer) containing base numbers 1 to 1487 of HCV RNA (the base numbers of RNA are indicated according to Kato et al., "Proc. Natl. Acad. Sci. USA, 87, 9524–9528 (1990)) was quantified from ultraviolet absorption at 260 nm, and then diluted to 1.0×10⁴ copies/5.0 μl with an RNA diluent (10 mM Tris-HCl (pH 8.0), 0.1 mM EDTA, 0.5 U/μl RNase Inhibitor). The diluent alone was used in a control test (Nega).

(2) Then, 20.8 μl of a reaction solution having the following composition was dispensed into each 0.5 ml PCR tube (trade name: Gene Amp Thin Walled Reaction Tubes, manufactured by Perkin Elmer), and 5.0 μl of the above RNA sample was added thereto.

Composition of the reaction solution (each concentration is a final concentration of the reaction system after the addition of the enzyme solution)

60.0 mM Tris-HCl buffer solution (pH 8.6)
13.0 mM magnesium chloride
110.0 mM potassium chloride
1.0 mM DTT
0.25 mM each dATP, dCTP, dGTP, dTTP
3.0 mM each ATP, CTP, UTP
2.25 mM GTP
3.6 mM ITP
1.0 μM each of a first primer and a second primer
0.16 μM of an oligonucleotide probe for cleavage (an oligonucleotide for cleaving the target RNA at the position where the first primer can bind, aminated at the 3' end)
39 U ribonuclease inhibitor (manufactured by Takara Shuzo)
15.0% DMSO
distilled water for adjusting the volume By the way, as the combination of the first and second primers and the probe for cleavage, any one of the following was used.

1. An oligonucleotide having a sequence described in SEQ ID NO: 11 (a promoter sequence of T7 polymerase of SEQ ID NO: 14 was added to the 5' end) as the first primer, an oligonucleotide described in SEQ ID NO: 6 as the second primer, and an oligonucleotide complementary to base numbers 651 to 700 of HCV RNA (containing the oligonucleotide described in SEQ ID NO: 3) as the probe for cleavage;

2. An oligonucleotide having a sequence described in SEQ ID NO: 11 (a promoter sequence of T7 polymerase of SEQ ID NO: 14 was added to the 5' end) as the first primer, an oligonucleotide described in SEQ ID NO: 7 as the second primer, and an oligonucleotide complementary to base By numbers 651 to 700 of HCV RNA (containing the oligonucleotide described in SEQ ID NO: 3) as the probe for cleavage;

3. An oligonucleotide having a sequence described in SEQ ID NO: 12 (a promoter sequence of T7 polymerase of SEQ ID NO: 14 was added to the 5' end) as the first primer, an oligonucleotide described in SEQ ID NO: 7 as the second primer, and an oligonucleotide complementary to base numbers 787 to 836 of HCV RNA (containing the oligonucleotide described in SEQ ID NO: 5) as the probe for cleavage;

4. An oligonucleotide having a sequence described in SEQ ID NO: 13 (a promoter sequence of T7 polymerase of SEQ ID NO: 14 was added to the 5' end) as the first primer, an oligonucleotide described in SEQ ID NO: 9 as the second primer, and an oligonucleotide complementary to base numbers 915 to 964 of HCV RNA (containing the oligonucleotide described in SEQ ID NO: 7) as the probe for cleavage;

5. An oligonucleotide complementary to base numbers 113 to 137 of HCV RNA (a promoter sequence of T7 polymerase of SEQ ID NO: 14 was added to the 5' end) as the first primer, an oligonucleotide complementary to base numbers 250 to 267 of HCV RNA as the second primer, and an oligonucleotide complementary to base numbers 71 to 120 of HCV RNA as the probe for cleavage.

(3) The above reaction solution was maintained at 41° C. for 5 minutes and then, 4.2 μl of an enzyme solution having the following composition maintained at 41° C. for 2 minutes beforehand was added thereto.

Composition of the enzyme solution (final concentration at the reaction)

1.7% sorbitol
8 units of AMV reverse transcription enzyme (manufactured by Takara Shuzo)
142 units of T7 RNA polymerase (manufactured by GIBCO)
3 μg of bovine serum albumin
distilled water for adjusting the volume (4) Successively, each PCR tube was maintained at 41° C. for 30 minutes, and then specific amplification products were analyzed by electrophoresis on a 4% agarose gel.

(5) After the electrophoresis, the gel was stained with a commercial staining solution (trade name: SYBR Green II, manufactured by Takara Shuzo).

Figure 2:
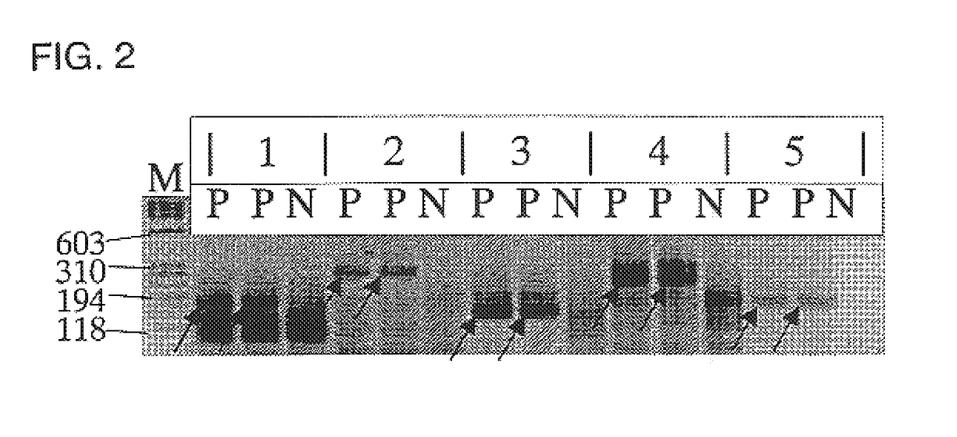
FIG. 2 shows results of RNA amplification reaction carried out with various combinations of the primers in Example 2. In the figure, P shows the cases that initial RNA amount of $10^4$ copies/5 μl was used as the RNA sample, and N shows the cases that the diluent alone was used instead of the RNA sample. Further, lane M is a molecular-weight marker, and the numbers 1 to 5 indicate numbers of the combination of the primer and probe shown in Example 2.

The results of the electrophoresis are shown in FIG. 2 (a photograph wherein black and white are reversed). In the cases of combinations (1 to 4) wherein the sequences of the invention were used, specific RNA amplification products having a dense darkness (indicated by arrows) were obtained in the systems to which HCV RNA was added. From these results, it was shown that these combinations of the oligonucleotide primers were useful for highly sensitive amplification and detection of HCV RNA.

EXAMPLE 3

Using combinations of oligonucleotide primers according to the invention, it was confirmed that specific detection of the target RNA, i.e., HCV RNA was possible.

(1) A sample of a standard RNA (1552 mer) containing base numbers 1 to 1487 of HCV RNA (the base numbers of RNA are indicated according to Kato et al., "Proc. Natl. Acad. Sci. USA, 87, 9524–9528 (1990)) was quantified from ultraviolet absorption at 260 nm, and then diluted to 1.0×10⁴ copies/5.0 μl or 1.0×10³ copies/5.0 μl with an RNA diluent (10 mM Tris-HCl (pH 8.0), 0.1 mM EDTA, 0.5 U/μl RNase Inhibitor).

(2) Then, 20.8 μl of a reaction solution having the following composition was dispensed into each 0.5 ml PCR tube (trade name: Gene Amp Thin Walled Reaction Tubes, manufactured by Perkin Elmer), and 5.0 μl of the above RNA sample (HCV RNA) was added thereto.

Composition of the reaction solution (each concentration is a final concentration of the reaction system after the addition of the enzyme solution)

60.0 mM Tris-HCl buffer solution (pH 8.6)
13.0 mM magnesium chloride
110.0 mM potassium chloride
1.0 mM DTT
0.25 mM each dATP, dCTP, dGTP, dTTP
3.0 mM each ATP, CTP, UTP
2.25 mM GTP
3.6 mM ITP 1.0 μM of a first oligonucleotide primer 1.0 μM of a second oligonucleotide primer 0.16 μM of an oligonucleotide probe for cleavage (an oligonucleotide for cleaving the target RNA at the position where the first primer can bind, aminated at the 3' end)

25.0 nM of an oligonucleotide probe labeled with an intercalative fluorescent pigment (FIG. 3) (HCV-YO, subjected to glycolic acid modification at the 3' end)

39 U ribonuclease inhibitor (manufactured by Takara Shuzo)

15.0% DMSO distilled water for adjusting the volume

By the way, as the combination of the primers and the probe, any one of the following was used.

1. An oligonucleotide having a sequence described in SEQ ID NO: 12 (a promoter sequence of T7 polymerase of SEQ ID NO: 14 was added to the 5' end) as the first primer, an oligonucleotide described in SEQ ID NO: 7 as the second primer, an oligonucleotide complementary to base numbers 787 to 836 of HCV RNA (containing an oligonucleotide described in SEQ ID NO: 5) as the probe for cleavage, and an oligonucleotide described in SEQ ID NO: 10 as the probe for detection;

2. An oligonucleotide complementary to base numbers 113 to 137 of HCV RNA (a promoter sequence of T7 polymerase of SEQ ID NO: 14 was added to the 5' end) as the first primer, an oligonucleotide complementary to base numbers 250 to 267 of HCV RNA as the second primer, an oligonucleotide complementary to base numbers 71 to 120 of HCV RNA as the probe for cleavage, and an oligonucleotide complementary to base numbers 223 to 233 of HCV RNA (tg sequence was added to the 3' end) as the probe for detection.

(3) The above reaction solution was maintained at 41° C. for 5 minutes and then, 4.2 μl of an enzyme solution having the following composition and maintained at 41° C. for 2 minutes beforehand was added thereto.

Composition of the enzyme solution (final concentration at the reaction)

1.7% sorbitol 8 units of AMV reverse transcription enzyme (manufactured by Takara Shuzo)

142 units of T7 RNA polymerase (manufactured by GIBCO)

Figure 3:
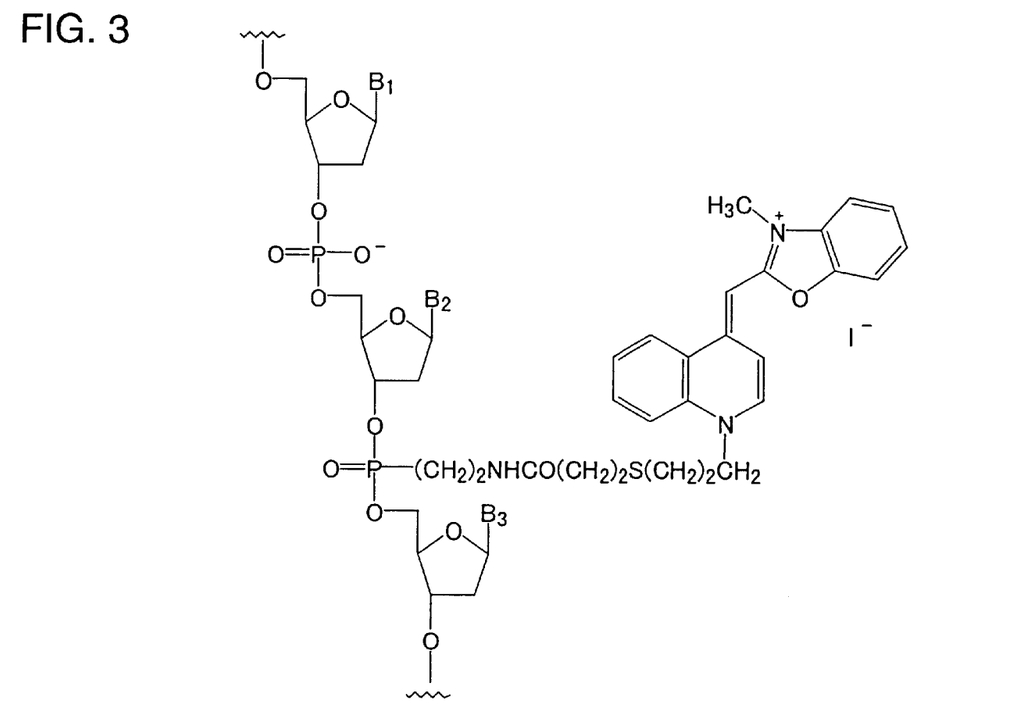
FIG. 3 shows the chemical structure of the intercalative fluorescent pigment of the oligonucleotide labeled with the intercalative fluorescent pigment used in Example 3.
Figure 4:
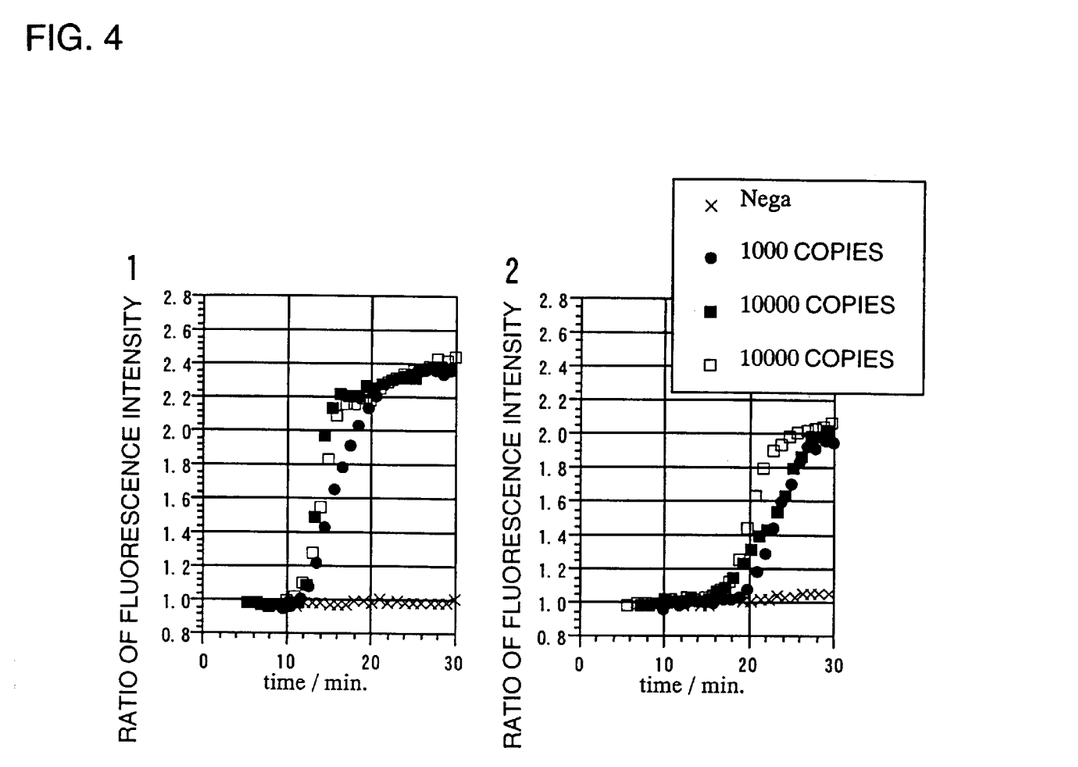

3 μg of bovine serum albumin distilled water for adjusting the volume (4) Successively, the fluorescent strength of each reaction solution was measured under maintaining at 41° C. at an excitation wavelength of 470 nm and fluorescent wavelength of 510 nm over the passage of time by means of fluorescent spectrometer capable of directly measuring the PCR tube and equipped with a temperature-controlling function. FIG. 3 shows the change of the ratio of fluorescent strength of each sample (value of fluorescent strength at a predetermined time/value of fluorescent strength of background) with the passage of time, the time when the enzyme was added being 0 minute.

In the case of combination 1 wherein the sequences of the invention were used, a specific and rapid fluorescent amplification was obtained in the systems to which HCV RNA was added as the target RNA. From the above, it was shown that the combination of the oligonucleotide of the invention enables a specific and highly sensitive amplification of HCV RNA.

As explained in the above, the oligonucleotide of the invention is an oligonucleotide which complementarily binds to HCV RNA even under the conditions of a relatively low temperature and a constant temperature (35 to 50° C., preferably 41° C.) wherein RNA may form an intramolecular structure, and binding of a primer or probe may be inhibited. Accordingly, it becomes possible to bind an oligonucleotide specifically without denaturation of the target RNA. Moreover, the oligonucleotide of the invention binds to HCV RNA specifically, and is useful as a combination of an oligonucleotide and an oligonucleotide probe for rapid amplification, and detection and identification of the target RNA.

Other than the above, with regard to the oligonucleotide of the invention, a sequence complementary to the above oligonucleotide is also useful for detecting cDNA obtainable by reverse transcription of HCV RNA, not limited to the RNA itself.

The base length of the oligonucleotide in the combination of the invention is not limited to the length described specifically, and the oligonucleotide includes oligonucleotides comprising at least 10 continuous bases in these sequences. This is apparent because a base sequence having about 10 mer is sufficient for attaining the specificity of a primer or probe with a target nucleic acid under a relatively low temperature (preferably 41° C.) condition.

While the invention has been described in detail and with reference to specific embodiments thereof, it will be apparent to one skilled in the art that various changes and modifications can be made therein without departing from the spirit and scope thereof.

This application is based on Japanese patent application No. 2000-334945 filed on Oct. 30, 2000, the entire contents thereof being hereby incorporated by reference.

What is claimed is:

1. An amplification step which comprises:

forming an RNA-DNA duplex by forming a cDNA by the action of an RNA-dependent DNA polymerase using a specific sequence of RNA from Hepatitis C virus in a sample as a template, a first primer having a sequence homologous to the specific sequence, and a second primer having a sequence complementary to the specific sequence (wherein either primer of the first or second primers has a sequence to which a promoter sequence of an RNA polymerase is added at the 5' end), forming a single-stranded DNA by degrading the RNA-DNA duplex by ribonuclease H, forming a double-stranded DNA having a promoter sequence for transcribing an RNA comprising the above RNA sequence or a sequence complementary to the above RNA sequence by a DNA-dependent DNA polymerase using the single-stranded DNA as a template, and forming an RNA transcription product from the double-strand DNA in the presence of an RNA polymerase, the RNA transcription product successively acting as a template for the formation of the single-stranded DNA by the above RNA-dependent DNA polymerase, wherein the oligonucleotide of SEQ ID NO: 11 is used as the first primer and the oligonucleotide of SEQ ID NO: 6 or 7 as the second primer; the oligonucleotide of SEQ ID NO: 12 is used as the first primer and the oligonucleotide of SEQ ID NO: 7 as the second primer; or the oligonucleotide of SEQ ID NO: 13 is used as the first primer and the oligonucleotide of SEQ ID NO: 9 as the second primer.

2. A method for detecting Hepatitis C virus comprising measurement of the fluorescent strength of a reaction solution, wherein the RNA-amplification step according to claim 1 is carried out in the presence of an oligonucleotide probe labeled with an intercalative fluorescent pigment, the sequence of the probe being complementary to at least part of the RNA transcription product, and the fluorescent characteristic of the probe being changed by the complementary binding to the RNA transcription product as compared with the case that the complex is not formed.

* * * * *

UNITED STATES PATENT AND TRADEMARK OFFICE
CERTIFICATE OF CORRECTION

PATENT NO.    : 6,756,198 B2
DATED         : June 29, 2004
INVENTOR(S)   : Toshiki Taya et al.

It is certified that error appears in the above-identified patent and that said Letters Patent is hereby corrected as shown below:

Title page,
Item [56], References Cited, U.S. PATENT DOCUMENTS, after "6,485,903" insert:
-- 5,747,244    5/1998      Sheridan et al.
   5,747,339    5/1998      Okayama et al.
   5,851,759    12/1998     Weiner
   6,001,990    12/1999     Wands et al. --
Insert:
-- FOREIGN PATENT DOCUMENTS
0 419 182       3/1991      European Pat. Off.
0 516 859       12/1992     European Pat. Off.
0 521 318       1/1993      European Pat. Off.
0 587 298       3/1994      European Pat. Off.
0 593 290       4/1994      European Pat. Off.
0 855 447       7/1998      European Pat. Off.
0 969 101       1/2000      European Pat. Off.
1 002 878       5/2000      European Pat. Off.
93/02103        2/1993      WIPO
96/10997        4/1996      WIPO
6-279500        10/1994     Japan
XP002265892     1/1993      Japan
XP002265893     11/1997     Japan
XP002265894     12/1993     Japan -- and
OTHER PUBLICATIONS, before "* cited by the examiner" insert:
-- Ishiguro, et al., "Homogeneous Quantitative Assay of Hepatitis C Virus RNA by Polymerase Chain Reaction in the presence of a Fluorescent Intercalater", Analytical Biochemistry, Vol. 229, No. 2, pp. 207-213, 1985.

Lima, et al., "Combinatorial Screening and Rational Optimization for Hybridization to Folded Hepatitis C Virus RNA of Oligonucleotides with Biological Antisense Activity", The Journal of Biological Chemistry, Vol. 272, No. 1, pp. 626-638, 1997.

UNITED STATES PATENT AND TRADEMARK OFFICE
CERTIFICATE OF CORRECTION

PATENT NO.    : 6,756,198 B2
DATED         : June 29, 2004
INVENTOR(S)   : Toshiki Taya et al.

It is certified that error appears in the above-identified patent and that said Letters Patent is hereby corrected as shown below:

OTHER PUBLICATIONS (cont'd),
  Kato, et al. "Molecular cloning of the human hepatitis C virus genome from Japanese patients with non-A, non-B hepatitis", Proceedings of the National Academy of Sciences of the USA, Vol. 87, No. 24, pp. 9524-9528, 1990. --

Signed and Sealed this

Ninth Day of November, 2004

JON W. DUDAS
*Director of the United States Patent and Trademark Office*

SEQUENCE LISTING

<160> NUMBER OF SEQ ID NOS: 14

<210> SEQ ID NO 1
<211> LENGTH: 21
<212> TYPE: DNA
<213> ORGANISM: Artificial Sequence
<220> FEATURE:
<223> OTHER INFORMATION: Oligonucleotide capable of binding to a specific site of HCV RNA

<400> SEQUENCE: 1
tttctttgag gtttaggatt t                                    21

<210> SEQ ID NO 2
<211> LENGTH: 23
<212> TYPE: DNA
<213> ORGANISM: Artificial Sequence
<220> FEATURE:
<223> OTHER INFORMATION: Oligonucleotide capable of binding to a
      specific site of HCV RNA

<400> SEQUENCE: 2
ttgccataga ggggccaagg gta                                  23

<210> SEQ ID NO 3
<211> LENGTH: 21
<212> TYPE: DNA
<213> ORGANISM: Artificial Sequence
<220> FEATURE:
<223> OTHER INFORMATION: Oligonucleotide capable of binding to a
      specific site of HCV RNA

<400> SEQUENCE: 3
tcgatgacct tacccaaatt a                                    21

<210> SEQ ID NO 4
<211> LENGTH: 20
<212> TYPE: DNA
<213> ORGANISM: Artificial Sequence
<220> FEATURE:
<223> OTHER INFORMATION: Oligonucleotide capable of binding to a
      specific site of HCV RNA

<400> SEQUENCE: 4
ggaatgtacc ccatgaggtc                                      20

<210> SEQ ID NO 5
<211> LENGTH: 20
<212> TYPE: DNA
<213> ORGANISM: Artificial Sequence
<220> FEATURE:
<223> OTHER INFORMATION: Oligonucleotide capable of binding to a
      specific site of HCV RNA

<400> SEQUENCE: 5
cagattccct gttgcatagt                                      20

<210> SEQ ID NO 6
<211> LENGTH: 20
<212> TYPE: DNA
<213> ORGANISM: Artificial Sequence
<220> FEATURE:
<223> OTHER INFORMATION: Oligonucleotide capable of binding to a
      specific site of HCV RNA

<400> SEQUENCE: 6
aagctaagag gaagatagag                                      20

<210> SEQ ID NO 7
<211> LENGTH: 20
<212> TYPE: DNA
<213> ORGANISM: Artificial Sequence
<220> FEATURE:
<223> OTHER INFORMATION: Oligonucleotide capable of binding to a
      specific site of HCV RNA

<400> SEQUENCE: 7
atacttgagt tggagcagtc                                      20

-continued

```
<210> SEQ ID NO 8
<211> LENGTH: 20
<212> TYPE: DNA
<213> ORGANISM: Artificial Sequence
<220> FEATURE:
<223> OTHER INFORMATION: Oligonucleotide capable of binding to a
      specific site of HCV RNA

<400> SEQUENCE: 8
ggtgtgcatg atcatgtccg                                              20

<210> SEQ ID NO 9
<211> LENGTH: 22
<212> TYPE: DNA
<213> ORGANISM: Artificial Sequence
<220> FEATURE:
<223> OTHER INFORMATION: Oligonucleotide capable of binding to a
      specific site of HCV RNA

<400> SEQUENCE: 9
gctgggagac gagaaaaacg ga                                           22

<210> SEQ ID NO 10
<211> LENGTH: 21
<212> TYPE: DNA
<213> ORGANISM: Artificial Sequence
<220> FEATURE:
<223> OTHER INFORMATION: Probe

<400> SEQUENCE: 10
gcggaagctg ggatggtcaa a                                            21

<210> SEQ ID NO 11
<211> LENGTH: 25
<212> TYPE: DNA
<213> ORGANISM: Artificial Sequence
<220> FEATURE:
<223> OTHER INFORMATION: Primer

<400> SEQUENCE: 11
gtcatcgata cccttacatg cggct                                        25

<210> SEQ ID NO 12
<211> LENGTH: 25
<212> TYPE: DNA
<213> ORGANISM: Artificial Sequence
<220> FEATURE:
<223> OTHER INFORMATION: Primer

<400> SEQUENCE: 12
ggaatctgcc cggttgctct ttctc                                        25

<210> SEQ ID NO 13
<211> LENGTH: 25
<212> TYPE: DNA
<213> ORGANISM: Artificial Sequence
<220> FEATURE:
<223> OTHER INFORMATION: Primer

<400> SEQUENCE: 13
tcaagtattg tgtatgaggc agcgg                                        25

<210> SEQ ID NO 14
<211> LENGTH: 28
<212> TYPE: DNA
```

```
<213> ORGANISM: T7 phase
<220> FEATURE:
<221> NAME/KEY: promoter
<222> LOCATION: (1)..(14)
<223> OTHER INFORMATION: Promoter sequence of T7 polymerase

<400> SEQUENCE: 14
aattctaata cgactcacta tagggaga                                          28
```